United States Patent [19]

Callens et al.

[11] Patent Number: 4,923,966
[45] Date of Patent: May 8, 1990

[54] USE OF GUANIDINE-RELATED COMPOUNDS COMPRISING A TETRAPHENYL-BORATE ION IN SOLUTION PHASE PEPTIDE SYNTHESIS

[75] Inventors: Roland Callens, Gent-Drongen; André Collin, Ligny, both of Belgium

[73] Assignee: Solvay & Cie (Société Anonyme), Brussels, Belgium

[21] Appl. No.: 207,876

[22] Filed: Jun. 17, 1988

[30] Foreign Application Priority Data

Jun. 19, 1987 [FR] France .................. 87 08695

[51] Int. Cl.$^5$ ............... C07K 1/02; C07K 1/06
[52] U.S. Cl. .................. 530/338; 530/335; 530/337
[58] Field of Search ............ 530/333, 335, 338, 337

[56] References Cited

PUBLICATIONS

Chemical Abstracts vol. 95, No. 4, Jul. 27, 1981.

*Primary Examiner*—Howard E. Schain
*Assistant Examiner*—Susan M. Perkins
*Attorney, Agent, or Firm*—Spencer & Frank

[57] ABSTRACT

Use of a guanidine-related compound in solution phase peptide synthesis, the guanidine-related compound comprising a tetraphenylborate ion and having the general formula:

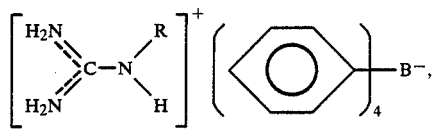

wherein R denotes an organic radical comprising at least one amine group.

4 Claims, No Drawings

USE OF GUANIDINE-RELATED COMPOUNDS COMPRISING A TETRAPHENYL-BORATE ION IN SOLUTION PHASE PEPTIDE SYNTHESIS

CROSS-REFERENCE TO RELATED APPLICATION

This application is related to copending application Ser. No. 07/207,877 filed June 17th, 1988.

BACKGROUND OF THE INVENTION

1. Field of the Invention

The present invention relates to guanidine-related compounds comprising a tetraphenylborate ion combined with a product comprising a guanidine groups, as well as a process for obtaining such compounds, which may be employed as means for dissolving the product in which the protection of the guanidine group is ensured, particularly during the synthesis of peptides from amino acids or peptides.

2. Description of the Related Art

German Patent Application DOS No. 2,716,477 discloses, in particular, N,N',N"-substituted guanidine salts of general formula:

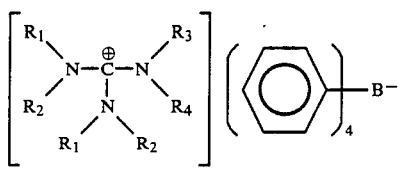

in which $R_1$, $R_2$, $R_3$ and $R_4$ denote an aliphatic, cyclic, arylated aliphatic, aromatic or heterocyclic radical, and in which only $R_1$ may be a hydrogen atom.

These products, which are protonated on the carbon atom of the substituted guanidine group, are synthesized from a halogenated derivative of carbamic acid and from substituted thiourea and may be employed as catalysts, plant protection agents and pharmaceutical dyes.

SUMMARY OF THE INVENTION

The present invention is aimed at providing a new class of compounds whose structural formula is close to that of the abovementioned products but in which all the valencies of the nitrogen atoms of the guanidine group save for one are saturated by hydrogen atoms.

The compounds according to the invention comprise a guanidine group and a tetraphenylborate ion and correspond to the general formula:

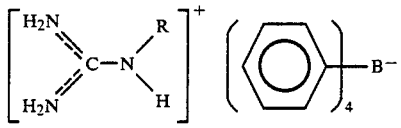

in which R denotes an organic radical containing at least one other amine group. R generally denotes a radical containing, in addition to an amine group, a carboxylic group, which groups may optionally be substituted.

Usually, R denotes a radical of general formula:

$$-X-CH-CO-Y$$
$$|$$
$$NH$$
$$|$$
$$A$$

in which X, A and Y denote, independently of each other, linear, branched or cyclic, substituted or unsubstituted, saturated or unsaturated aliphatic radicals, aromatic radicals, arylated aliphatic radicals or heterocyclic radicals. A may additionally also denote a hydrogen atom and Y a hydroxyl group or a halogen atom.

Generally,

X denotes a linear, branched or cyclic, substituted or unsubstituted, saturated or unsaturated aliphatic radical containing up to 25 carbon atoms, A denotes a hydrogen atom, an aliphatic or aromatic radical containing heteroatoms or otherwise, such as protecting groups or activating groups, one or more amino acids linked by peptide bonds, in which certain groups are optionally substituted by protecting groups or activating groups;

Y denotes a hydroxyl group, a halogen atom, or an aliphatic or aromatic radical optionally containing heteroatoms, such as protecting groups or activating groups, an amino group, an amino acid or a peptide in which some groups are optionally substituted by protecting groups or activating groups as well as by amino groups of general formula $NR_1R_2$ in which $R_1$ and $R_2$ independently of each other denote a hydrogen atom or an alkyl group containing 1 to 3 carbon atoms.

Preferably:

X denotes an alkyl radical of general formula $-(CH_2)_n-$ in which n is an integer between 1 and 10, A denotes a hydrogen atom, an amino acid, a peptide or a protecting group, Y denotes a hydroxyl group, a protecting group, an activating group, an amino acid or a peptide.

In a very particularly preferred manner:

X denotes the radical $-(CH_2)_n-$ in which n is between 1 and 6,

A denotes a hydrogen atom, a protecting group such as particularly benzyloxycarbonyl (Z) or tert-butyloxycarbonyl (t-Boc), an amino acid or a peptide, which are optionally substituted by these same protecting groups, and Y denotes a hydroxyl group, a protecting group such as a benzyl ester, an activating group such as N-hydroxysuccinimide, or an amino acid or a peptide which are optionally substituted by protecting and/or activating groups or an amino group.

Lastly, good results have been obtained when:

X denotes the radical $-(CH_2)_3-$,

A denotes a hydrogen atom, an optionally substituted amino acid or a protecting group such as benzyloxycarbonyl or tert-butyloxycarbonyl and Y a hydroxyl group or an optionally substituted amino acid.

A amino acid means any organic acid containing at least one carboxylic group and at least one primary or secondary amine group, such as the known natural amino acids or synthetic amino acids. A peptide means any peptide originating from any combination of natural or synthetic amino acids.

A protecting groups means any compound mentioned for this purpose in the literature and more particularly by:

M. Bodanszky, Principles of Peptide Synthesis, 1984, volume 16, Reactivity and Structure Concepts in Organic Chemistry, M. Bodanszky, A. Bodanszky, the Practice of Peptide Synthesis, 1984, volume 21, Reactivity and Structure Concepts in Organic Chemistry.

By way of illustration, the following protecting groups may be employed in the compounds of the invention:

acyl-type protecting groups such as especially formyl, trifluoroacetyl, phthaloyl, 4-toluenesulphonyl, benzenesulphonyl and 2-nitrophenylsulphenyl, aromatic urethane-type protecting groups such as especially substituted or unsubstituted benzyloxycarbonyl such as p-chlorobenzyloxycarbonyl, p-nitrobenzyloxycarbonyl, p-bromobenzyloxycarbonyl, p-methoxybenzyloxycarbonyl, benzhydryloxycarbonyl, 2-(4-biphenylyl)propyl(2)oxycarbonyl, 2-(3,5-dimethyloxyphenyl)propyl(2)oxycarbonyl, and triphenylphosphonoethyloxycarbonyl, aliphatic urethane-type protecting groups such as especially tert-butyloxycarbonyl, diisopropylmethoxycarbonyl, isopropyloxycarbonyl, ethoxycarbonyl, allyloxycarbonyl, 9-fluorenylmethyloxycarbonyl, 2-methylsulphonylethyloxycarbonyl and 2,2,2-trichloroethyloxycarbonyl, cycloalkyl urethane-type protecting groups such as especially cyclopentyloxycarbonyl, adamantyloxycarbonyl, cyclohexyloxycarbonyl, tert-amyloxycarbonyl and isobornyloxycarbonyl, thiourethane-type protecting groups such as especially phenylthiocarbonyl, alkyl-type protecting groups such as especially triphenylmethyl (trityl) and benzyl, trialkylsilane groups such as trimethylsilane, and alkoxy groups such as especially methyl ester, ethyl ester, tert-butyl ester and benzyl ester.

An activating groups means any known or unknown activating group, such as those mentioned in the literature and more particularly in the papers by:

M. Bodanszky,

M. Bodanszky and A. Bodanszky, referred to above.

Usually, an oxycarbonyl, oxycarboxyl, N-oxyimidoyl, imidazoyl such as especially pivaloyloxycarbonyl, N-hydroxysuccinimidoyl, dicyclohexylcarbodiimidoyl or 4-nitrophenyl ester group is employed as an activating group.

The preferred compounds according to the invention correspond to the formulae:

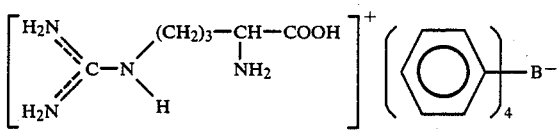

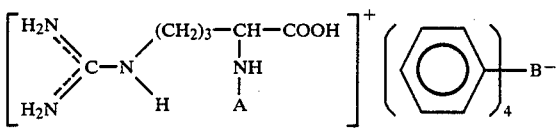

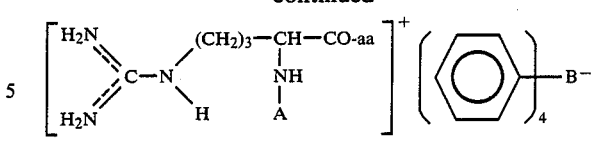

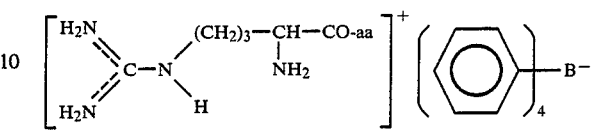

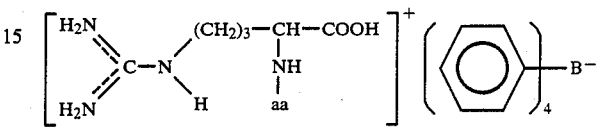

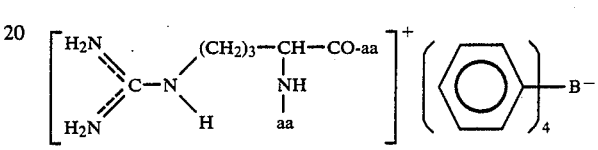

in which aa denotes an amino acid or a peptide linked by a peptide bond to arginine and in which the amine and carboxylic groups are optionally protected or substituted. A protection of this kind is made necessary when certain functional groups, in particular amine or carboxylic, must be blocked to prevent their being involved in subsequent reactions when the compound is employed. The carboxylic end group of certain amino acids or peptides may additionally be substituted by an amino group such as the $-NH_2$ or $-NH-CH_2-CH_3$ group.

In a particularly preferred manner, aa denotes an amino acid.

The compounds according to the invention may be prepared by any suitable organic synthesis combining known or unknown reactions and applying generally or particularly to a single specified compound or to a class of compounds.

A process which has yielded good results in the preparation of the compounds according to the invention consists in employing a tetraphenylborate salt and a product comprising a guanidine group.

The tetraphenylborate salts employed for the synthesis of the compounds according to the invention may be formed by any inorganic or organic base.

An organic base and more particularly a nitrogenous organic base such as a secondary, tertiary or heterocyclic amine is usually employed. Good results have been obtained with triethylamine, diisopropylethylamine, N-methylmorpholine, N-ethylmorpholine, N-methylpiperidine, N-ethylpiperidine, tri-n-butylamine, dicyclohexylamine and imidazole.

The tetraphenylborate salt is employed in the reaction in the presence of a solvent or of a mixture of solvents. A single polar organic solvent such as especially dimethyl sulphoxide (DMSO), N,N-dimethylformamide (DMF), N-methylpyrrolidone or acetonitrile is generally employed. A solvent which has given good results is N,N-dimethylformamide.

The quantity of tetraphenylborate salt employed may vary with wide limits. From 20 to 1 mole of tetraphenylborate salt is generally employed per mole of product containing the guanidine group. From 10 to 1 mole of tetraphenylborate salt is preferably employed. In a particularly preferred manner, 1 mole of tetraphenylborate salt is employed per mole of product containing the guanidine group.

The other operating conditions employed in the process for preparing the compounds according to the invention are not critical for the invention. Thus, the pressure at which the process is performed is generally between 0.1 and 10 bars and good results have been obtained at atmospheric pressure. The temperature at which the process is performed is usually between −60° and 100° C. and may vary depending on the nature of the reactants and the compound which it is ultimately intended to prepare.

The process may be carried out in any apparatus designed for this purpose.

The compounds of the invention can be employed as intermediates in chemical synthesis.

Because of their solubility in organic solvents they may be used particularly when they themselves couple with other products; in particular, in the synthesis of peptides from amino acids, particularly as described in European Patent Application No. 0,184,243, which relates to a process involving a trialkylcyanosilane.

Furthermore, the fact that the tetraphenylborate ion is the counterion of the guanidine group, which is protects, makes it possible to ensure the protection of this guanidine group during the formation of selective couplings and thus to obtain products of higher purity during the synthesis. In fact, at the end of the peptide synthesis, the tetraphenylborate ion is easily displaced from the product containing the guanidine group by any known method, for example by the addition of water, and this makes it possible, on the one hand, to release the guanidine group and, on the other hand, to re-form the initial tetraphenylborate salt. This salt can thus be recovered and recycled when the reaction medium is not acidic.

More particularly, the invention relates to the use of the tetraphenylborate ion as a means for dissolving arginine and peptides containing arginines which are free but which are protonated in the side chain, in organic solvents.

DESCRIPTION OF THE PREFERRED EMBODIMENT

The examples which follow are used to illustrate the invention.

In these examples, the following abbreviations have been employed:

| | |
|---|---|
| Arg | arginine |
| Gly | glycine |
| Leu | leucine |
| Pro | proline |
| O-Piv | pivaloyloxy (trimethylacetyloxy) |
| O-Succ | N-hydroxysuccinimide |
| Z | benzyloxycarbonyl-type protecting group |
| t-Boc | tert-butyloxycarbonyl-type protecting group |
| DMF | N,N-dimethylformamide |
| Et | ethyl group —$CH_2$—$CH_3$. |

EXAMPLE 1

Synthesis of the compound formed by arginine and tetraphenylborate 8.71 g (0.050 mole) of protonated arginine (H-arg OH), 23.18 g (0.055 mole) of triethylammonium tetraphenylborate, and then 100 ml of N,N-dimethylformamide (DMF), are introduced in succession into a 250-ml thermostated reactor fitted with a condenser and a stirring system.

The mixture is maintained at 25° C. at atmospheric pressure with vigorous stirring for 5 minutes.

A concentration of 0.397 mole per kg of a compound formed by arginine and tetraphenylborate is obtained.

This mixture may be employed directly for the synthesis of the peptide t-Boc-Leu-Arg OH.

EXAMPLE 2

Use of the compound formed by arginine and tetraphenylborate in the synthesis of the peptide t-Boc-Leu-Arg OH (a) Synthesis of the peptide t-Boc-Leu-Arg OH 17.57 g (0.054 mole) of leucine (Leu) whose amine group is protected by the tert-butyloxycarbonyl (t-Boc) group and whose carboxylic group is activated by N-hydroxysuccinimide are added in solid form to the mixture obtained in Example 1 and maintained at 25° C.

After 4 hours at 25° C. the reaction solution contains the dipeptide t-Boc-Leu-Arg-OH obtained with a degree of coupling of about 100%.

(b) Isolation of triethylammonium tetraphenylborate 900 ml of water are introduced into a 2-l thermostated reactor fitted with a condenser, a dropping funnel and a stirring system. The temperature is brought to 5° C.

Using the dropping funnel, the reaction solution containing the dipeptide t-Boc-Leu-Arg OH is added over 30 minutes with vigorous stirring, while the temperature is maintained between 5° and 10° C.

Triethylammonium tetraphenylborate precipitates progressively over 1 hour at 5° C. The precipitate is separated off by filtration through a porosity 4 sintered disc and is washed with 4 50-ml portions of water.

After drying at 50° C. at a reduced pressure of 1 mb, 22.95 g of triethylammonium tetraphenylborate are recovered, i.e. 99% of the quantity employed.

(c) Extraction and purification of the peptide t-Boc-Leu-Arg OH

The filtrate and the washings containing t-Boc-Leu-Arg OH are concentrated in a rotary evaporator at 60° C. and at a reduced pressure of 1 mb until a residue of approximately 20 g is obtained.

The residue is treated with 400 ml of acetone at ambient temperature in a reactor fitted with a stirring system. The residue disperses slowly and gives rise to a white precipitate.

After 2 hours of treatment with vigorous stirring, the suspension obtained is kept at 5° C. for 24 hours.

The precipitate formed is then separated off by filtration through a porosity 4 sintered disc and is washed with 4 20-ml portions of acetone.

After drying at 40° C. at a reduced pressure of 1 mb, 17.5 g of a pulverulent white solid are recovered, whose content of dipeptide t-Boc-Leu-Arg is 95%, i.e. an 86% yield of pure dipeptide.

EXAMPLE 3

Synthesis of the compound formed by tetraphenylborate and arginine protected with a benzyloxycarbonyl group 1500 ml of DMF, 154 g (0.5 mole) of arginine whose α-amino group is protected with a benzyloxycarbonyl group (Z-Arg) and 210.5 g (0.5 mole) of triethylammonium tetraphenylborate are introduced in succession into a 2-l thermostated reactor fitted with a condenser and a stirring system.

The mixture is heated to 40° C. with vigorous stirring for 1 hour at atmospheric pressure. The solution obtained is the cooled to −20° C. and is stored at this temperature.

A concentration of 0.280 mole per kg of compound formed by tetraphenylborate and arginine whose α-amino group is protected by a benzyloxycarbonyl group is obtained.

EXAMPLE 4

Synthesis of the dipeptide Z-Arg-Pro

Use of the compound obtained in Example 3

(a) Synthesis of the dipeptide Z-Arg-Pro 69 g (0.6 mole) of proline and 119 g (1.2 mole) of trimethylcyanosilane are introduced in succession into a 250-ml thermostated reactor (I) fitted with a condenser, a stirring system and a device allowing a nitrogen gas blanket to be maintained and connected to a sodium hydroxide scrubber.

The mixture is heated to 40° C. for 5 minutes with stirring. The solution obtained (sol I) is homogeneous and is stored at ambient temperature.

200 ml of DMF, 67 g (0.55 mole) of pivaloyl chloride (Piv-Cl) and 44 g (0.55 mole) of pyridine are introduced in succession into another 3-l thermostated reactor (II) fitted with a condenser, a stirring system, a device permitting a nitrogen gas blanket to be maintained and connected to a sodium hydroxide scrubber and a dropping funnel.

This solution is brought to −30° C.

The solution obtained in Example 3 is then introduced with vigorous stirring over 10 minutes by means of the dropping funnel while the temperature of the reaction mixture is maintained between −30° and −15° C.

This reaction mixture is maintained at −15° C. for 5 minutes.

The solution (sol I) is then introduced over 5 minutes. The reaction solution is kept stirred at −15° C. for 1 hour and then at 0° C. for 2 hours.

The degree of coupling is in the region of 85%.

(b) Isolation of the triethylammonium tetraphenylborate salt 5 l of water cooled to 5° C. are introduced into a 10-l thermostated reactor (III) equipped in the same way as reactor (II), followed by the reaction solution, over 60 minutes.

The mixture is kept at 5° C. with good stirring; the triethylammonium tetraphenylborate salt precipitates gradually.

After 1 hour the precipitate is separated off by filtration through a porosity 4 sintered disc and is washed with 4 250-ml portions of water.

After drying at 50° C. under a reduced pressure of 1 mb, 209 g of triethylammonium tetraphenylborate salt are recovered, i.e. more than 99% of the quantity employed.

(c) Extraction and purification of the dipeptide

The filtrate and the washings are concentrated in a rotary evaporator at 40° C. at a reduced pressure of 1 mb until a residue of approximately 300 g is obtained.

This residue is dissolved in 1 l of water and the pH is adjusted to 7.5 at ambient temperature by gradual addition of triethylamine until it is stable.

The dipeptide Z-Arg-Pro precipitates gradually in zwitterion form.

After 2 hours the precipitate is separated off by filtration through a porosity 4 sintered disc.

The precipitate is washed with 4 20-ml portions of water and is then dried at a reduced pressure of 1 mb.

In this manner, 130 g of a pulverulent white solid are recovered, whose content of dipeptide Z-Arg-Pro is close to 100° C., i.e. an 85% yield of pure product.

EXAMPLE 5

Synthesis of the compound formed by tetraphenylborate and the protected dipeptide Z-Arg-Pro 200 ml of DMF, 20.3 g (0.050 mole) of the protected depeptide Z-Arg-Pro as obtained in Example 4, and 19.4 g (0.050 mole) of imidazolidinium tetraphenylborate are introduced in succession into a 500-ml reactor fitted with a condenser and a stirring system.

The solution becomes clear after 1 hour's stirring at ambient temperature and atmospheric pressure.

A concentration of 0.220 mole per kg of the compound formed by tetraphenylborate and the protected dipeptide Z-Arg-Pro is obtained.

EXAMPLE 6

Synthesis of Z-Arg-Pro-NH-Et

Use of the compound obtained in Example 5

10.1 g (0.063 mole) of carbonyldiimidazole dissolved in 60 ml of DMF are added to the solution obtained in Example 5. The reaction mixture is placed at ambient temperature with stirring for 90 minutes.

12.2 g (0.150 mole) of ethylamine hydrochloride dissolved in 100 ml of DMF are then added. The reaction solution is placed at ambient temperature for 15 hours with stirring, the reaction being then terminated.

The reaction solution is then concentrated in a rotary evaporator at 50° C. at a reduced pressure of 1 mb until a residue of approximately 100 g is obtained.

The residue is taken up with 800 ml of water. The solution obtained is extracted twice with a mixture of 350 cm$^3$ of ethyl acetate and 150 cm$^3$ of ethyl ether. After phase separation, the organic phases are evaporated to dryness in a rotary evaporator at 40° C. at a reduced pressure of 1 mb.

A residue of 34.3 g is recovered. It consists essentially of the compound formed by the peptide Z-Arg-Pro-NH-Et and tetraphenylborate, and the coupling efficiency is therefore greater than 90%.

The exchange of the tetraphenylborate anion with the acetate anion may be carried out by treating the peptide in solution in a water-methanol mixture (in a proportion of ½) on an anionic resin of the Bio Rad AG 1×8 type, acetate form.

EXAMPLE 7

Synthesis of the compound formed by tetraphenylborate and the peptide t-Boc-Leu-Arg-Pro 300 ml of DMF, 50.8 g (0.105 mole) of the peptide t-Boc-Leu-Arg-Pro and 40.6 g (0.105 mole) of imidazolidinium tetraphenylborate are introduced in succession into a 1-l reactor fitted with a condenser and a stirring system.

The mixture is stirred for 10 minutes at ambient temperature at atmospheric pressure. A homogeneous solution is then obtained.

It contains a concentration of 0.280 mole per kg of compound formed by tetraphenylborate and the peptide t-Boc-Leu-Arg-Pro.

EXAMPLE 8

Synthesis of the peptide t-Boc-Leu-Arg-Pro-Gly NH$_2$

Use of the compound obtained in Example 7

19.5 g (0.120 mole) of carbonyldiimidazole dissolved in 100 ml of DMF are added to the homogeneous solution obtained in Example 7.

The mixture is stirred for 100 minutes at ambient temperature.

82.8 g (0.210 mole) of protonated glycine amide tetraphenylborate salt dissolved in 200 ml of DMF are added to it. This reaction solution is stirred at ambient temperature for 15 hours.

57.8 g (0.420 mole) of triethylamine hydrochloride dissolved in 3 l of water are introduced into a 5-l thermostated reactor fitted with a condenser, a stirring system and a dropping funnel.

Using the dropping funnel, the reaction solution is added over 30 minutes with vigorous stirring while the temperature is kept between 5° and 10° C. Triethylammonium tetraphenylborate precipitates gradually.

After 1 hour at 5° C. the precipitate is separated off by filtration through a porosity 4 sintered disc and is washed with 4 30-ml portions of water.

After drying at 50° C. at a reduced pressure of 1 mb, 131.3 g of triethylammonium tetraphenylborate are recovered, corresponding to 99% of the quantity of tetraphenylborate ion employed.

The filtrate and the washings are concentrated in a rotary evaporator at 50° C. at a reduced pressure of 1 mb until a residue of 200 g is obtained.

This residue contains 49.4 g (0.091 mole) of peptide t-Boc-Leu-Arg-Pro-Gly-NH$_2$, i.e. a coupling efficiency of 87%.

What is claimed is:

1. Use of a guanidine-related compound in solution phase peptide synthesis, the guanidine-related compound comprising a tetraphenylborate ion and having the general formula:

wherein R denotes an organic radical comprising at least one amine group.

2. Use of a guanidine-related compound in solution phase peptide synthesis, the guanidine-related compound comprising a tetraphenylborate ion and having the general formula:

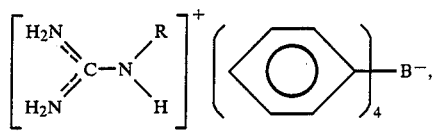

wherein R denotes an organic radical comprising at least one amine group, and a carboxylic group, at least one of which at least one amine group and carboxylic group may be substituted.

3. Use of a guanidine-related compound in solution phase peptide synthesis, the guanidine-related compound comprising a tetraphenylborate ion and having the general formula:

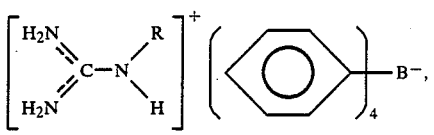

wherein R denotes an organic radical comprising at least one amine group and a carboxylic group, at least one of which at least one amine group and carboxylic group may be substituted, and have the general formula:

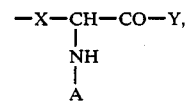

in which X, A and Y denote, independently of each other, linear, branched or cyclic, substituted or unsubstituted, saturated or unsaturated aliphatic radicals, aromatic radical, arylated aliphatic radicals or heterocyclic radicals, and in which A may also denote hydrogen and Y may also denote a hydroxyl group or halogen.

4. Use of a guanidine-related compound in solution phase peptide synthesis, the guanidine-related compound comprising a tetraphenylborate ion, and having the general formula:

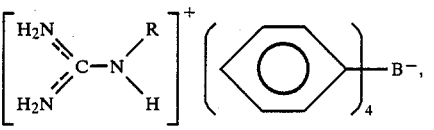

wherein R denotes an organic radical comprising at least one amine group and a carboxylic group, at least one of which at least one amine group and carboxylic group may be substituted, and having the general formula:

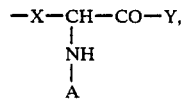

in which X, A and Y, independently of each other, linear, branched or cyclic, substituted or unsubstituted, saturated or unsaturated aliphatic radicals, aromatic radicals, arylated aliphatic radicals or heterocyclic radicals, and in which A may also denote hydrogen and Y may also denote a hydroxy group or halogen, and
wherein X denotes a $-(CH_2)-_3$ radical, A denotes hydrogen, an optionally substituted amino acid or a protecting group such as a benzyloxy-carbonyl group or a tert-butyloxycarbonyl group, and Y denotes a hydroxyl group or an optionally substituted amino acid.

* * * * *